United States Patent [19]

Meline et al.

[11] Patent Number: 4,884,456
[45] Date of Patent: Dec. 5, 1989

[54] HIGH TEMPERATURE EXTENSOMETER SYSTEM

[75] Inventors: Harry R. Meline, Minnetonka; Scott P. Iverslie, Crystal, both of Minn.

[73] Assignee: MTS Systems Corporation, Eden Prairie, Minn.

[21] Appl. No.: 186,367

[22] Filed: Apr. 26, 1988

[51] Int. Cl.⁴ .......................... G01B 5/30; G01N 3/08; G01N 17/00

[52] U.S. Cl. ........................................ 73/826; 33/787; 374/55

[58] Field of Search .............. 374/55, 47, 49; 73/826, 73/781, 855; 33/147 D, 787, 788, 789, 790

[56] References Cited

U.S. PATENT DOCUMENTS

| | | | |
|---|---|---|---|
| 2,336,286 | 12/1943 | Owen | 374/55 |
| 2,545,482 | 3/1951 | Manjoine et al. | 33/785 |
| 3,001,291 | 9/1961 | Sjostrom | 338/6 X |
| 3,254,741 | 6/1966 | Greene, Jr. | 73/430 X |
| 3,385,097 | 5/1968 | Green | 374/55 |
| 3,960,009 | 6/1976 | Roepke et al. | 73/784 X |
| 4,522,066 | 6/1985 | Kistler et al. | 338/6 X |
| 4,525,081 | 6/1985 | Myhre | 73/430 |
| 4,527,335 | 7/1985 | Meline | 33/787 |
| 4,535,636 | 8/1985 | Blackburn et al. | 73/831 |
| 4,537,082 | 8/1985 | Meline et al. | 33/787 X |
| 4,607,531 | 8/1986 | Meline et al. | 73/794 |

OTHER PUBLICATIONS

MTS—"Grips and Fixtures Catalog", ASTM E8, pp. 1–31 (in brochure), MTS System Corporation, 1986.

*Primary Examiner*—Daniel M. Yasich
*Attorney, Agent, or Firm*—Kinney & Lange

[57] ABSTRACT

A high temperature extensometer system carries specimen contact rods of substantial length which pass through openings in a furnace to engage a specimen in such furnace. The rods are supported at the exterior of the furnace on a parallelogram linkage support frame made to provide an output indicating specimen strain as the contact rods separate and also made with parallel beams which shift so the rods can move differentially in longitudinally axial direction. The rods shift axially when the specimen and test loading grips shift in position, for example when the grips and specimen are initially heated.

25 Claims, 5 Drawing Sheets

HIGH TEMPERATURE EXTENSOMETER SYSTEM

BACKGROUND OF THE INVENTION

1. Field of the Invention

The present invention relates to a support system for a high temperature extensometer which must accommodate shifts in the specimen contact rods used for sensing strains in a specimen as the specimen and test assembly are subjected to high temperatures.

2. Description of the Prior Art

High temperature extensometers have been used for years, and generally are used in connection with a furnace that will heat a specimen to a desired level, and which specimen is then subjected to loads to determine specimen properties. The strain is sensed by having long ceramic rods which engage the specimen at contact points and extend to sensor system supports that are remote and shielded from the furnace. The extensometers provide an indication of the amount of strain in the specimen. In the prior art, the elongated rods and sensor systems were supported on the specimen and cantilevered outwardly. The rods were shorter than those now required with new higher temperature furnaces.

With longer rods external supports for the extensometer are needed. The supports have to be shielded from heat, and be made to avoid placing loads on the sensing rods, and thus must permit substantially unrestrained movement in several degrees of freedom to accommodate shifts in the specimen during the process of heating up.

SUMMARY OF THE INVENTION

The present invention relates to a high temperature extensometer support system which supports an extensometer assembly having specimen contact rods of substantial length, and which support system accommodates movement of these rods during initial warm-up of the specimen and testing apparatus in a furnace for the high temperature test and yet provides accurate measurements of specimen strain. The specimen contact rods are also called extension rods, and are of substantial length so they pass through openings in the furnace to engage a specimen in the furnace. The rods are supported on the exterior of the furnace. Shifts in the specimen position as it heats up, due to thermal expansion of various parts, including the grips holding the specimen, are accommodated by providing a parallelogram linkage support frame for the specimen contact rods. One of the specimen contact rods is supported relative to the parallelogram linkage support frame through a sensing system which senses differential movement between the outer ends of the specimen contact rods when the specimen is under strain. The other of the rods is supported independently of the sensing system with respect to the parallelogram linkage support frame.

The parallelogram linkage support frame is made so the rods can move differentially in their longitudinal axial direction without causing any undue loads on the rods and without placing any unwanted strains in the sensing system, itself. The specimen contact rods are urged axially toward the specimen under a spring load. The linkage or hold down flexure system for providing this axial load on the specimen contact rods in direction toward the specimen permits the rods to move differentially in axial direction and twist relative to each other generally about an axis lying in the direction of the longitudinal axis of one of the rods without causing the rods to slip off the specimen and without causing unwanted signals from the sensing system.

The entire parallelogram linkage support frame is supported relative to a load frame supporting the specimen through a flexure link which permits the entire support frame to move easily in direction parallel to the longitudinal axes of the elongated specimen contact rods.

The parallelogram linkage support frame is made up of first and second spaced, parallel beams, parallel to the specimen contact rods, and third and fourth connecting beams joining the first and second beams. The third and fourth beams are connected at their ends through spring flexures (no friction, zero clearance hinges) to the first and second beams. The parallelogram linkage support frame will permit movement of the first and second beams in direction of their longitudinal axes (which remain parallel). The flexure link for the support frame is connected to one of the beams and extends upwardly to where it is supported relative to the main test load frame. The flexure link can be adjusted in vertical direction so that the parallelogram support frame is supported at a reference position when the specimen contact rods are properly located. At this position the parallelogram linkage support frame is a rectangle, that is the first and second beams are perpendicular to the third and fourth beams. Suitable stops are provided to prevent extensive pivoting movement of the parallelogram linkage support frame.

In the form shown, the plane of the parallelogram linkage support frame is vertical and parallel to the specimen axis (or loading axis) so the first and second beams are at the top and bottom of the support frame. The first and second specimen contact rods are connected to the first and second beams of the parallelogram support frame, and the supports are made rigid in direction of the axes of the contact rods and the axes of the first and second beams, which are mutually parallel to the rods at reference position.

The first contact rod is coupled to the first (top) beam and the axes of the first rod and first beam are parallel. The mounting is such that the first rod axis will not move or tilt about an axis perpendicular to the specimen axis.

The second specimen contact rod is supported on the second beam through a sensing system mounting for sensing differential movement between the outer ends of the first and second specimen contact rods. The sensing system measures strain in direction of the specimen axis and as the second contact rod pivots at its base end relative to the second (bottom) beam about an axis perpendicular to the end specimen axis. The support of the base of the second specimen contact rod is rigid against pivoting about an axis parallel to the specimen axis relative to the second beam of the support frame.

In a preferred embodiment, the mounting of the first specimen contact rod is, however, made to permit movement of the first rod about an axis parallel to the specimen axis to accommodate some twisting of the specimen.

The hold down flexure system for providing an axial load on the elongated specimen contact rods comprises a prebent spring, and a selected arrangement of laterally extending spring straps that will permit the outer ends of the specimen contact rods to separate relative to each other, and to twist in torsion as permitted by the base end mounting of the rods, and also to permit the entire parallelogram linkage support frame to move as needed.

Suitable counterweights are provided to counterbalance the moments created by gravity on the second specimen contact rod about the mounting axis of the second rod, which is coupled through a sensing system to tee second beam. The sensing system mounting for the second or bottom specimen contact rod is used to provide a signal indicating differential movement between the outer ends of the specimen engaging ends of the specimen contact rods.

The parallelogram linkage support frame also is counterweighted to avoid unwanted moments and balance the support frame in its reference position.

The parallel linkage support frame is adapted to suit a wide variety of extensometer arrangements, particularly for high temperature operation. The plane of the parallelogram linkage support frame can be positioned perpendicular to a plane defined by the axes of the specimen contact rods if desired, rather than parallel to such plane, as shown.

BRIEF DESCRIPTION OF THE DRAWINGS

FIG. 5 is a fragmentary side view similar to that shown in FIG. 3 illustrating the top portion of the parallelogram linkage support frame, and the suspension system from the fixed support with a furnace location illustrated in dotted lines, but not to scale;

DETAILED DESCRIPTION OF THE PREFERRED EMBODIMENTS

Figure 1:
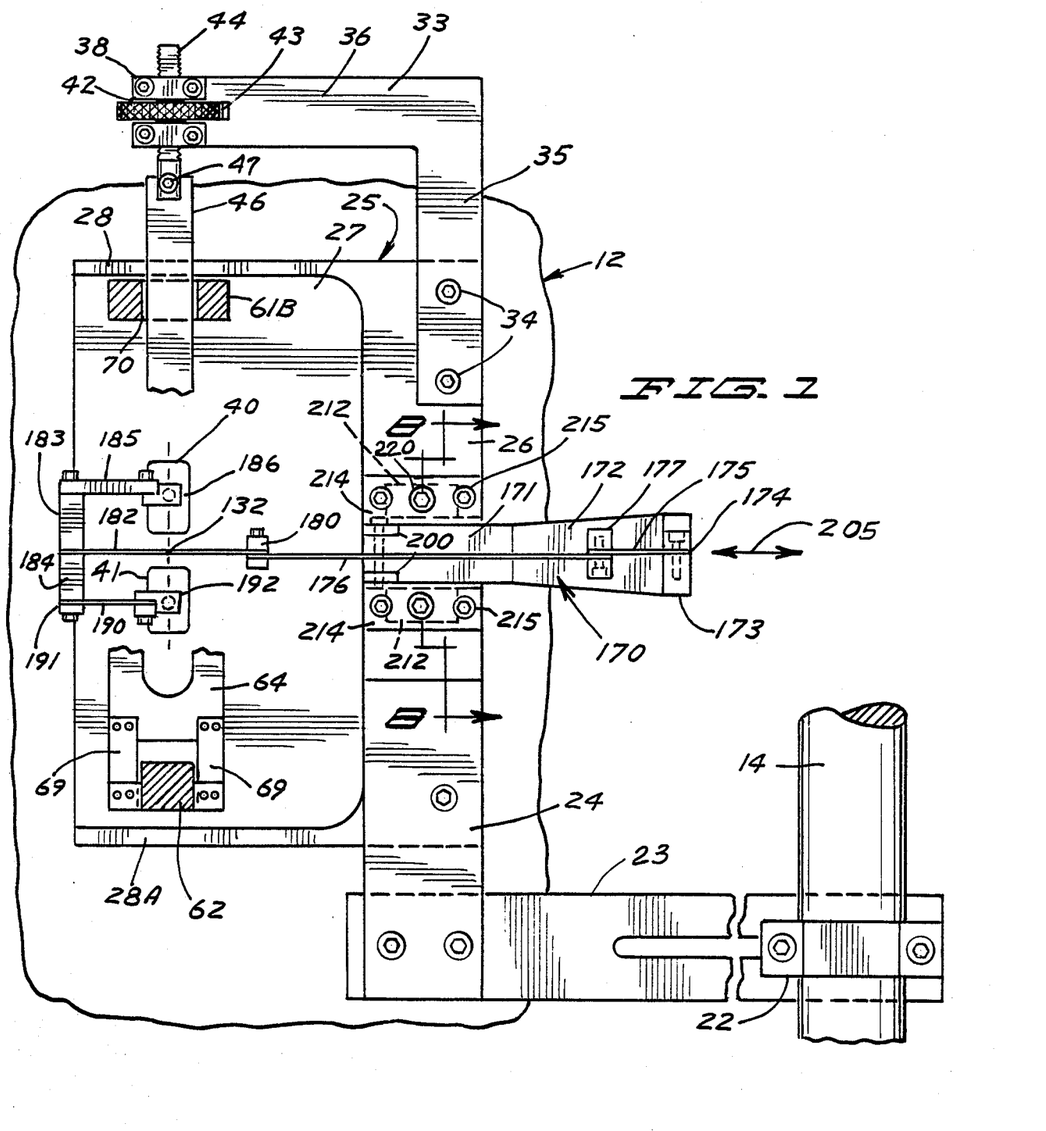
FIG. 1 is a fragmentary elevational view, looking toward an associated test furnace, of a typical heat shield and main support for a high temperature extensometer made according to the present invention with parts shown fragmentarily.
Figure 2:
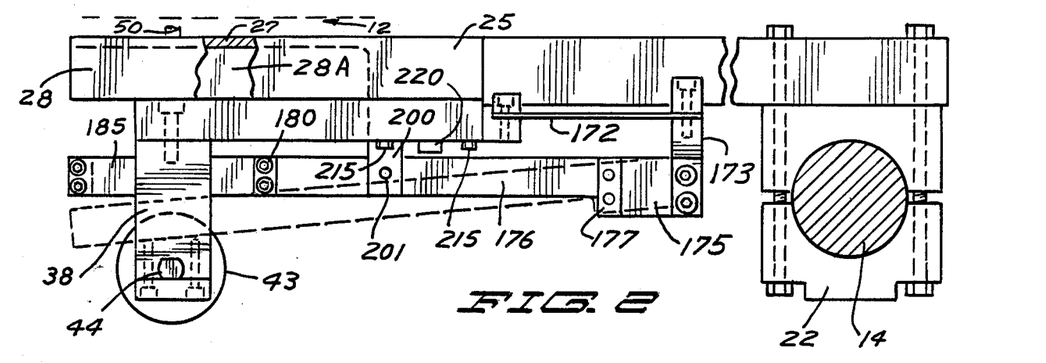
FIG. 2 is a top plan view of the device of FIG. 1 with a phantom representation of an associated test furnace illustrated, but not to scale.
Figures 3, 4:
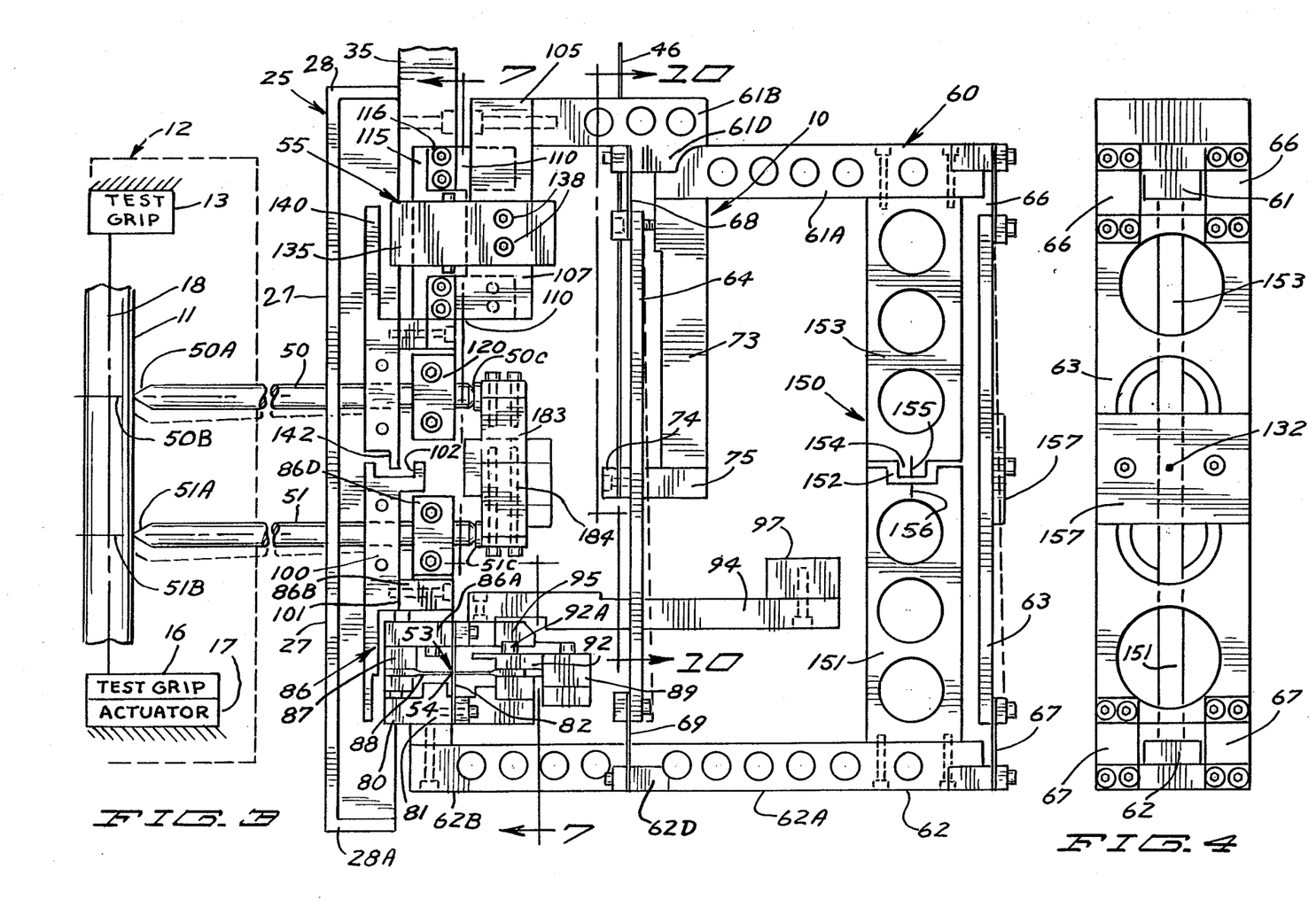
FIG. 3 is a side view of a parallelogram linkage support frame made according to the present invention supported from the main support shown in FIGS. 1 and 2 and showing elongated specimen contact rods engaging a specimen that is mounted in a furnace.
FIG. 4 is a rear view of the device of FIG. 3.

Referring to the drawings and the numerals of reference thereon, an extensometer assembly is indicated generally at 10 in FIG. 3, and it is of a type that is used to test a specimen indicated at 11 that is mounted adjacent to a heat source, such as being in a furnace represented in dotted lines at 12 in FIGS. 2 and 3 and schematically represented in FIG. 1. The furnace 12 has suitable openings for operation with the extensometer and with a test load frame or testing machine. The furnace 12 is mounted with respect to a load frame comprising a pair of columns 14, one of which is shown only fragmentarily in FIGS. 1 and 2. A first specimen grip 13 (FIG. 3) is mounted on the load frame and a second load grip 16 is attached to an actuator 17 (FIG. 3) for loading the specimen 11 along its central axis 18 in the load frame. The extensometer assembly 10 is supported so that the strain sensing is accurate and so that the specimen contact rods that contact the specimen are not likely to slip when the specimen 11 and the grips 13 and 16 move as the furnace is heated, or when the specimen 11 is loaded. In FIGS. 1 and 2, the main support is illustrated, fragmentarily. The column 14 forming part of the test load frame is used as a mounting member, and a split clamp indicated generally at 22 is clamped onto the column 14 and can be adjusted up and down. The split clamp in turn is used to support a support arm 23 that extends radially from the column. The arm 23 would be at an angle with respect to a line extending between a pair of columns 14 that are normally used in a load frame because the furnace 12 and specimen 11 are positioned between the load frame columns and the main part of the extensometer assembly 10 is outside the furnace.

The arm 23 in turn supports an upright support block 24 that is attached to the arm 23 at its outer end as seen in FIGS. 1 and 2. The support block 24 is suitably attached to a unitary heat shield indicated at 25. The heat shield 25 is made of a suitable heat conducting material such as copper, and has internal passageways for cooling water. The heat shield 25 is made with a relatively thick side block 26, and a heat shield plate 27 that is attached to the block 26. The plate 27 has upper and lower flanges 28 and 28A, respectively (see FIGS. 5 and 6 also). The plate 27 is also shown in FIG. 2 in partial section, and the lower flange 28A can be seen where the upper flange 28 is broken away.

Additionally, an extensometer main support arm assembly indicated generally at 33 is mounted to the upper end of the block 26 with suitable cap screws 34. The extensometer support arm assembly 33 has an upright portion 35, and a laterally extending portion 36 that extends above the adjacent plate 27. A laterally extending arm 38 forming part of the arm assembly 33 is fixed to portion 36 and extends in a direction generally perpendicular to the plate 27. The arm 38 is positioned in alignment with a pair of apertures indicated at 40 and 41 in plate 27, which are used for permitting elongated specimen contact rods 50 and 51 (FIGS. 2, 3, 5, 6 and 7) to pass through the heat shield into the furnace 12 to contact the specimen 11 being tested. The outer end of arm 38 has a horizontal slot 42 milled in it (FIG. 1). A knurled thumb wheel or nut 43 is placed in the slot 42, and a screw 44 is threaded in the knurled nut. The screw 44 has flat sides, and passes through openings in the arm 38 on opposite sides of the slot in which the knurled nut 43 is mounted. The screw 44 therefore will not rotate, but can be moved axially up or down by rotating the knurled nut. The lower end of the screw 44 is bifurcated to receive a thin flexure support strap 46. The strap 46 is held on the end of the screw 44 with a cross pin 47 (FIG. 1). This also can be seen in FIG. 5, where the flexure strap 46 is shown along with the screw 44 and the knurled nut 43. The arm assembly 33 including the upright section 35 and the lateral section 36 is a unitary member that stably support overhead support arm 38.

The heat shield 25, which is supported stably on support block 24 and arm 23 from the load frame column 14 thus provides the main support for supporting the extensometer assembly 10.

Referring to FIG. 3, it can be seen that the extensometer assembly 10 includes a pair of elongated specimen contact rods 50 and 51. The first rod 50 is the upper rod as shown, and the second rod 51 is the lower rod. The outer ends 50A and 51A of the rods contact a specimen with an edge line or knife edge formed by suitably shaping the ends.

The lower specimen contact rod 51 is supported through a measuring sensor or sensing system indicated generally at 53 that is of substantially conventional design utilizing a cross flexure arrangement so that the rod 51, and in particular its outer end 51A, which is the specimen contact end, can pivot and move along the axis 18 of the specimen 11 relative to the outer end 50A of the rod 50 about a flexure pivot axis indicated generally at 54. The upper specimen contact rod 50 is supported on a contact rod support system 55, which comprises a cross-flexure arrangement for mounting the base end of the rod 50 for permitting movement of the outer end 50A of the specimen contact rod 50 about an axis generally parallel to the axis 18 of the specimen to be tested.

The support system 55 and the sensing system 53 which support the inner or base ends of the rods 50 and 51 are supported by a parallelogram linkage support frame indicated generally at 60, which includes a first link or beam 61 which as shown is an upper beam, and a second (lower) link or beam 62. The first and second beams 61 or 62 have beam sections 61A and 62A which are mounted parallel to each other, and which are held together with a third link or beam 63 and a fourth link or beam 64, which is parallel to the third beam 63. The third and fourth beams are joined to the first and second beams 61 and 62 to form the parallelogram linkage support frame 60. The beams 61 and 62 are to the third link 63 through a first flexure strap set 66 that comprises a pair of spaced apart coplanar spring straps that are flexible and which are joined at first ends to an end of first beam section 61A, and at second ends to the end of third beam 63. The opposite end of the third beam 63 is connected with a pair of flexible straps or flexures 67 to the outer end of the second beam section 62A Straps 67 are fastened at their ends to the second beam section 62A and the third beam 63, respectively. The fourth beam 64 is connected with suitable flexure straps 68 to ears 61D integral with the first beam section 61A at an intermediate portion of the beam 61. The ears form the end of the first parallel link or beam section 61A. The lower end of the fourth link or beam 64 is connected with a pair of coplanar flexure straps 69 to a pair of ears 62D at an intermediate portion of the beam 62, which ears are at the end of second beam section 62A.

It can be seen therefore that the first and second (upper and lower) beams 61 and 62 can move axially independently of each other in direction parallel to the longitudinal axes 50B and 51B of the elongated specimen contact rods 50 and 51 as permitted by the hinging or pivoting action of the flexure straps 66, 67, 68 and 69. The straps form friction free, zero clearance (or looseness) hinges.

The upper beam section 61A forms the actual parallel beam or link that is connected to the third and fourth beams 63 and 64. A second arm or beam section 61B of beam 61 is integral with the parallel beam section 61A and extends toward the specimen and heat shield from the beam section 61A. The beam or arm section 61B has a substantially greater lateral width than the beam section 61A, as shown perhaps best in FIG. 6, and has a central opening therethrough indicated at 70.

It should be noted that the beams of the parallelogram linkage support frame 60 have cross holes formed therein for weight reduction. These holes are seen in FIG. 3, for example.

The flexure support strap 46 passes through this opening 70, and the lower end of strap 46 is mounted to a parallel linkage support frame arm 73 with a suitable clamp block 74 held in place with cap screws. The arm 73 has a base portion 75 (FIG. 3) which passes through an opening in the fourth beam or link 64. The arm 73 is positioned between the beams or links 63 and 64 as can be seen and is near the center of gravity of the extensometer assembly 10, so the assembly can be balanced when suspended from the support strap 46. The strap 46 bends very easily about a transverse or horizontal pivot axis. The upper end of the support arm 73 is fixed to the first beam section 61A with suitable cap screws.

The flexure straps 68 are mounted on the ears 61D that are integral with the beam section 61B and on the lower side of the beam section 61B. The ears 61D extend laterally from the width of the beam section 61A. Flexure strap 46 permits relatively free movement of the entire parallelogram support frame linkage and the supported specimen contact rods 50 and 51 in direction parallel to the axes 50B and 51B of the specimen contact rods. The support strap 46 also will twist easily about its longitudinal axis which is parallel to the plane of the parallelogram linkage support frame.

The second beam section 62A corresponds to and is parallel to and aligned with the first beam section 61A of the first beam 61, and an arm section 62B of beam 62 extends outwardly toward the heat shield 25 and specimen beyond the fourth beam 64. The end of second beam section 62B adjacent the heat shield 25 supports the sensing system 53, which in turn supports the elongated specimen contact rod 51.

Figures 7, 8:
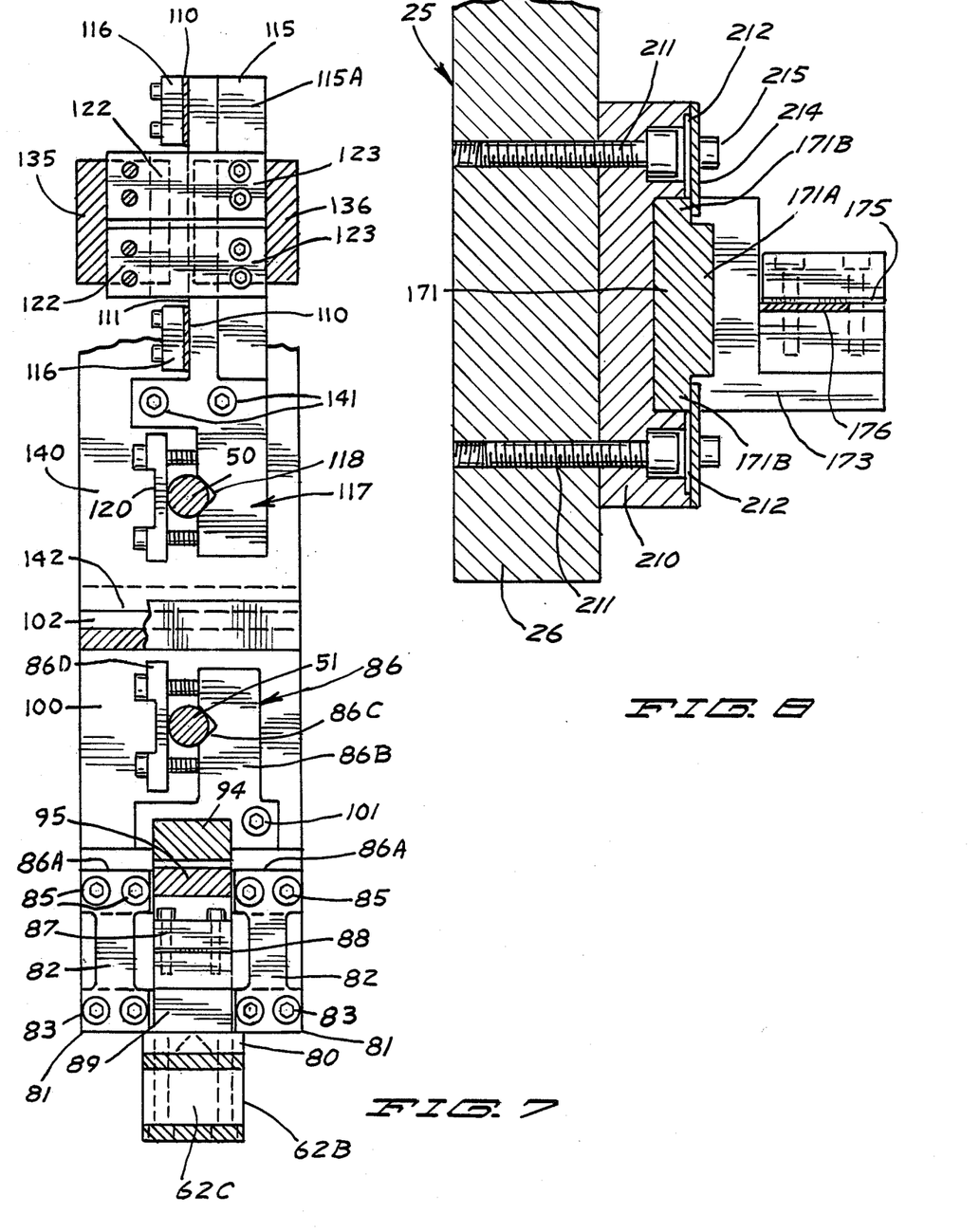
FIG. 7 is a sectional view taken as on line 7—7 in FIG. 3.
FIG. 8 is an enlarged sectional view taken as on line 8—8 in FIG. 1.
Figure 8:
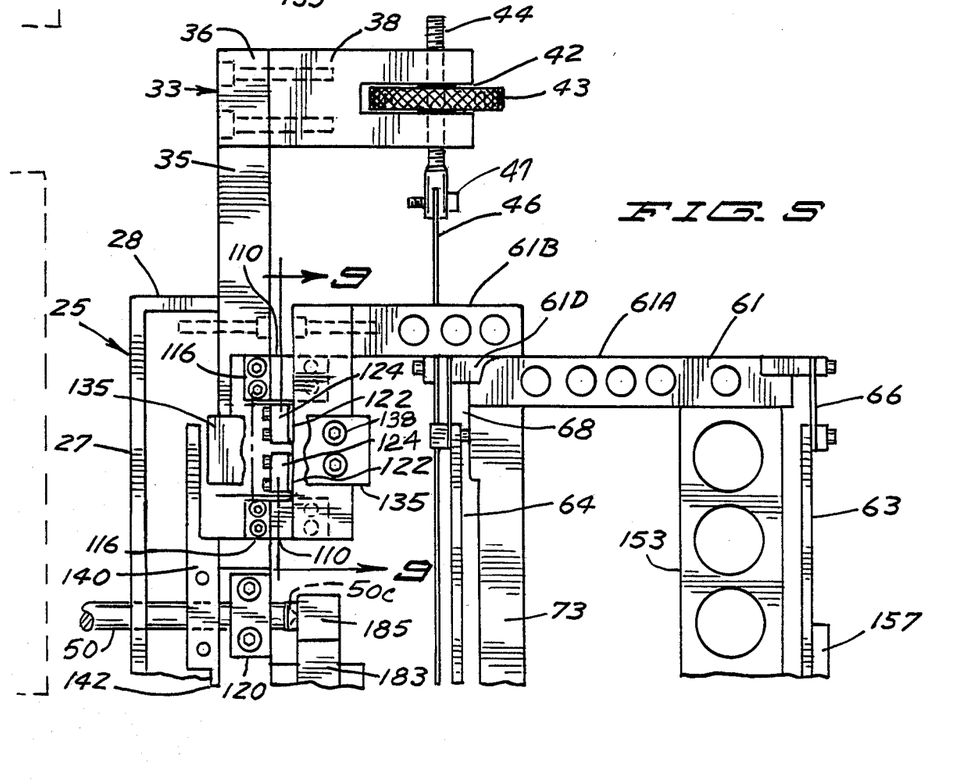

The sensing system 53 has two relatively movable members joined by a separate, pivot forming cross-flexure of substantially conventional design. The sensing system 53 includes a base member 80 that is fixedly connected to the beam section 62B and is spaced slightly thereabove. The base member 80 has a pair of ears 81 extending laterally of the beam section 62B (see FIG. 7) and each of these ears 81 supports a separate flexure strap 82. First ends of the straps 82 are fastened to the ears 81 with suitable cap screws 83. As can be seen in FIG. 7 these straps 82 are spaced apart. The upper ends of the straps 82 are connected with cap screws 85 to a lower specimen contact rod support arm 86, which has a wide portion 86A on which the flexure straps 82 are attached with the cap screws 85. The specimen contact rod support arm 86 has an upright column portion 86B extending in direction toward the specimen contact rod 51. A V-shaped receptacle 86C is formed on a side of column 86B for centering and receiving the base end of specimen contact rod 51, and clamping the rod 51 in place with a suitable clamp plate 86D.

Additionally, the specimen contact rod support arm 86 has a lower center portion 87 that is substantially centered between the flexure straps 82, and extends down below the attachment points of the cap screws 85. This center portion 87 supports one end of a flexure strap 88 that is a single strap that passes generally horizontally between the straps 82, so that the planes of the straps 82 and straps 88 intersect along the pivot axis indicated at 54. One end of the flexure strap 88 is connected to the block or center portion 87 of the arm assembly 86, and the opposite end of the flexure strap 88 is supported on a center support 89 formed on the arm 80, positioned between the ears 81, and thus extending between the flexure straps 82,82, back over a portion of the arm section. 62B. The end of the flexure strap 88 that is attached to the center support 89 is held in place with a suitable clamp block 92 and cap screws 92A.

The specimen contact rod 51 thus can pivot about axis 54 relative to the arm section 62B and the rest of the parallelogram linkage support frame. The flexure strap 88 has strain gages thereon to measure the bending of the strap and provide an output signal indicating movement of the over end of rod 51 relative to the arm (and relative to rod 50 in direction of the loading axis) 62B using known circuitry. Thus, the sensing system 53 is used to indicate relative movement of the rods 50 and 51 in direction of the loading axis of the specimen.

The support arm 86 also has a counterweight arm 94 mounted thereto on the top portion of a center block 95 fixed on the arm 86. The block 95 extends rearwardly above the clamp block 92 and is positioned so that it can move between the cap screws 92A that hold the block 92 in position to permit the required pivotal movement of arm 86 and rod 51 about pivot axis 54.

The counterweight arm 94 extends through an opening in the fourth beam 64 of the parallelogram linkage support frame and can move a limited amount up and down as the specimen contact rod 51 moves, which will in turn cause pivoting at axis 54 and thus movement of the block 95 and the counterweight arm 94. A counterweight 97 is provided at the outer end of the arm 94, and the counterweight 97 can be adjustable in size or mass, as well as in position in longitudinal direction, to properly counterweight the elongated specimen contact rod 51.

A secondary heat shield indicated generally at 100 in FIGS. 3 and 7 is attached to the contact rod support arm 86, at junction line 101, and extends upwardly above the end of the support arm past the specimen contact rod 51. The heat shield 100 has a transverse receptacle 102 formed at the upper end which provides an interface with a secondary mating heat shield for the upper specimen contact rod. The heat shield 100 has an opening through which the specimen contact rod 51 extends. This opening in heat shield 100 for rod 51 can closely clear the rod 51 because the rod 51 does not move relative to the opening or heat shield 100. This close fit helps block heat being radiated through the opening in the main heat shield wall 27 that is provided for the specimen contact rod 51.

The upper or reference specimen contact rod 50 is mounted on a flexure support that permits rod 50 to pivot about an axis parallel to axis 18 of the specimen 11, but rod 51 is rigidly mounted to the parallel linkage support frame 60 in relation to movement parallel to the axis 18. Thus specimen movement along axis 18 will cause movement of rod 51 relative to rod 50.

Figures 9, 10:
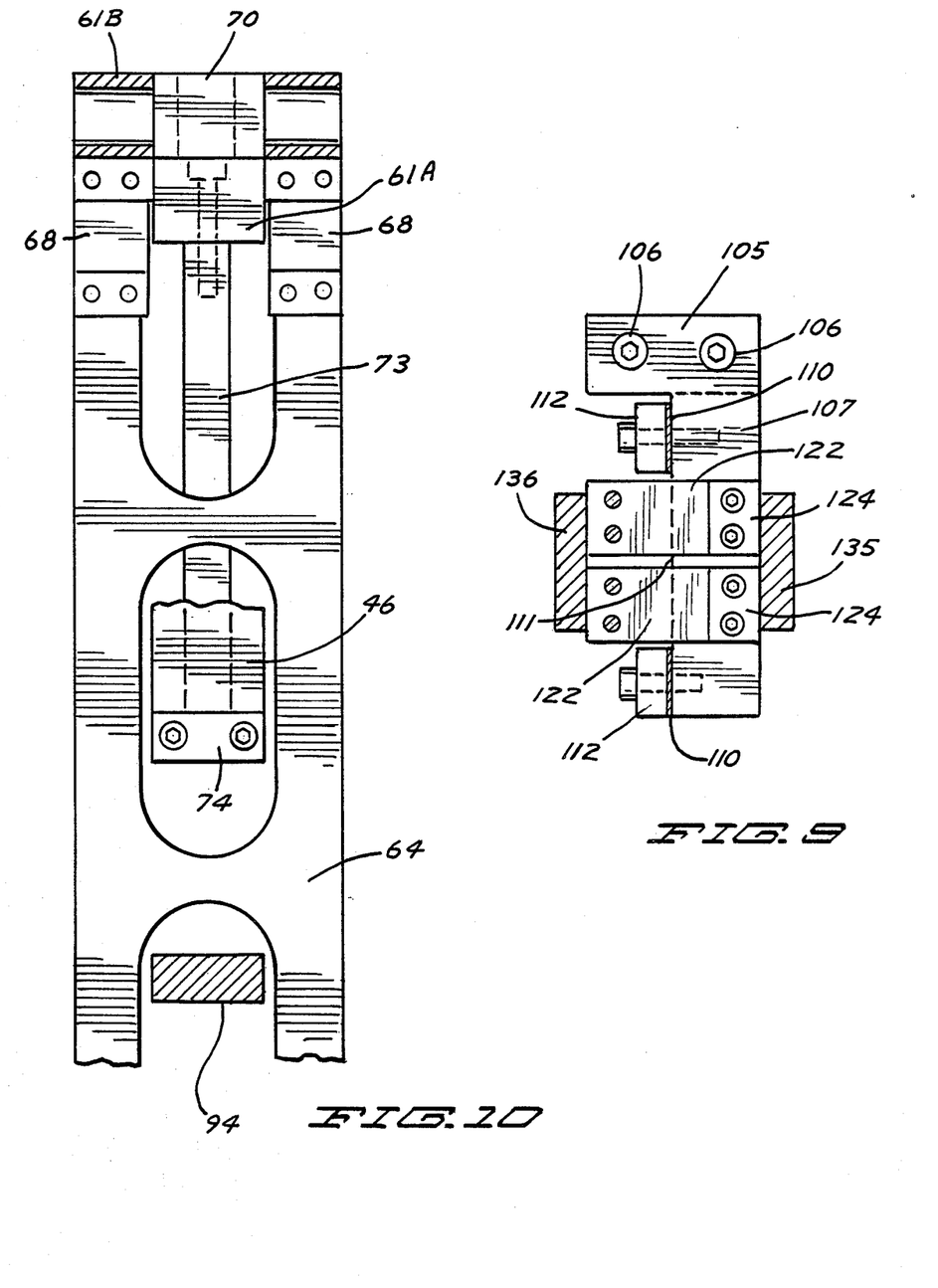
FIG. 9 is an enlarged fragmentary sectional view taken as on line 9—9 in FIG. 5.
FIG. 10 is a sectional view taken on line 10—10 in FIG. 3.

The specimen contact rod 50 is supported by the support flexure assembly 55, which perhaps can be best seen in FIGS. 3, 5, 6, 7 and 9. The arm or beam section 61B of beam 61 extending from the parallel beam section 61A has a depending support block 105 that is fixed to the end of the arm section 61B and extends therefrom toward second beam 62. As can be seen in FIG. 9, this support block 105 has a head portion held with cap screws 106 onto the end of the arm section 61B, and has a narrow leg 107 depending downwardly from the head portion. The leg 107 has a surface 111 that is approximately at the center of the beam 61. The leg 107 supports a pair of vertically spaced flexure straps 110 against surface 111, and these flexure straps are held clamped against the surface 111 with suitable clamp blocks 112 held in place with cap screws. The flexure straps 110 extend forwardly (toward heat shield 25) as shown in FIG. 3 and are clamped onto an arm 115 with suitable clamp blocks 116.

Figure 6:
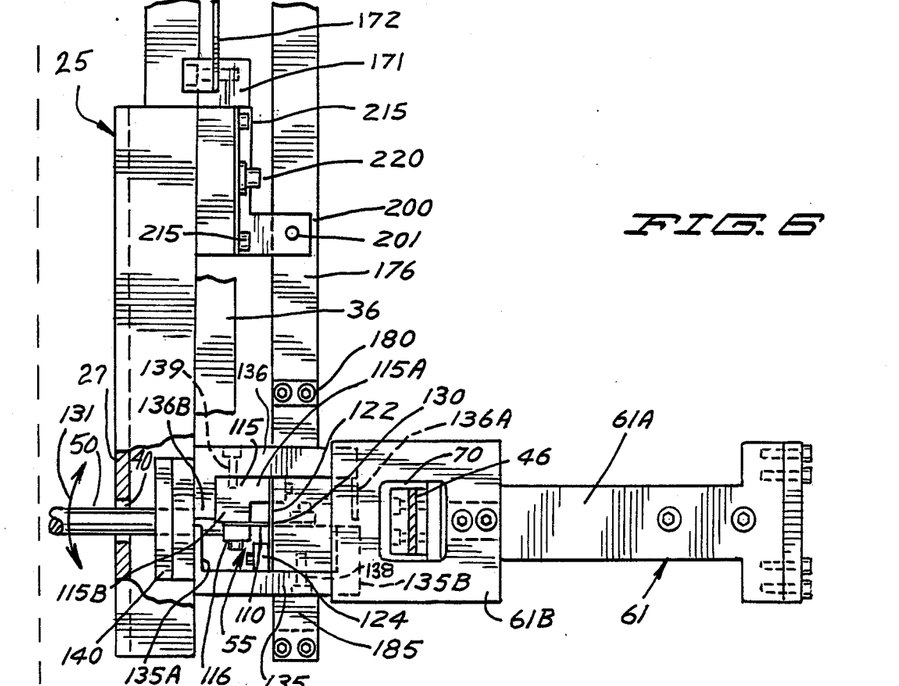
FIG. 6 is a top plan view of the device of FIG. 5.

The arm 115 has a lower end portion 117 that has a V-block surface 118 (FIG. 7) for receiving the specimen contact rod 50, and the rod 50 is clamped in place with a suitable clamp plate 120 held in place with cap screws. The arm 115 is thus supported on the flexure straps 110 with respect to the surface 111 of the leg portion 107 of the support block 105. The arm 115 is L-shaped as viewed from the top, as can be seen in FIG. 6, and has a leg portion 115A that provides a surface at right angles to the surface 111. Leg 115A supports a pair of flexure straps 122 thereon. The straps 122 are positioned between straps 110 as can be seen in FIG. 7, and also in FIG. 9. The flexure straps 122 have planes at right angles to the planes of flexure straps 110. The flexure straps 122 are clamped to leg 115A with clamp blocks 123.

FIG. 7 and FIG. 9 are taken on sight lines in opposite directions along substantially the same plane. The flexure straps 122 are mounted with respect to a forward surface of the leg 107 with suitable clamp blocks 124 as can be seen in FIG. 9, as well as being supported with respect to the rearwardly facing surface of the leg 115A with suitable clamp blocks 123.

Thus, the two sets of flexure straps 110 and 122 intersect along a pivot axis shown in FIG. 6 at 130 and this permits the specimen contact rod 50 to move or pivot about axis 130 in directions as indicated by the arrow 131 in FIG. 6.

The amount of pivoting about axis 130 is to accommodate slight torsional movement of the specimen or the parallelogram linkage support frame 60. The weight of the specimen contact rods 50 and 51, the supports for the specimen contact rods, and the parallelogram linkage support frame 60 is supported from the flexure strap 46. The strap 46 restrains any tendency of the support frame 60 and other portions of the extensometer assembly to pivot about an axis that is generally parallel to the contact rods 50 and 51 and at their base ends is midway therebetween, and which is shown by the dot 132 in FIGS. 1 and 4. The axis of torsion or twist actually is about on a line from the point of contact of rod 51 with specimen 18 at end 51B to the point 132 midway between the rods at the base ends of the rods. The flexure strap 46 has a width that is adequate to resist movement about the axis 132.

The support block 105 and the arm 115 carry cooperating stops that will prevent excessive movement of specimen contact rod 50 about axis 130. The two stops are mirror images of each other and are indicated at 135 and 136, respectively. These stops are generally channel-shaped as perhaps can best be seen in FIG. 6, and each one has a narrow stop leg 135A and 136A, respectively, and a wider stop leg 135B and 136B, respectively. The stop 135 is clamped onto the outer side surface of the leg 107 of the block 105 with suitable cap screws 138, and the stop 136 is clamped onto the side surface of the arm 115 with suitable cap screws shown at 139 in FIG. 6. The stop legs 136A and 135B are spaced slightly at the rear, underneath the arm section 61B and the legs 136B and 135A are spaced slightly apart at the forward side of the arm 115. The adjacent pairs of legs contact after limited pivotal movement of the specimen contact rod 50 about axis 130.

A secondary heat shield 140 is clamped with cap screws 141 to the arm 115. Heat shield 140 has a lip 142 at its lower end that fits into the receptacle 102 of the heat shield 100, to provide an overlap for heat shielding. Again, the heat shield 140 has a relatively close fitting opening for the specimen contact rod 50 because the heat shield 140 is directly and fixedly attached to the arm supporting the rod 50 so that it moves with the rod.

A stop assembly 150 is provided at the rear portion of the parallelogram linkage support frame, and in particular extends between the first beam or link section 61A, and the second beam link section 62A. The stop assembly 150 includes an upright column 151 that is fixed to the second beam section 62A with suitable cap screws, and the upright column 151 has a recess or receptacle 152 formed therein at the upper ends. A second stop column 153 is fixed to the first beam section 61A, and depends therefrom. The second stop column is in alignment with the stop column 151 as can be seen in FIG. 4. The stop column 153 has a lug 154 which fits into the receptacle 152, and thus the lug 154 will strike the front or rear surface defining the receptacle 152 if the parallelogram linkage support frame moves too far out of a rectangular configuration, which is when right angles are formed between the axis of first and second parallel beam sections 61A and 62A and the third and fourth beams 63 and 64.

Additionally, there are scribe marks 155 on the lug 154, and a corresponding center line scribe mark 156 on the column 151 adjacent receptacle 152, which will align when the parallelogram linkage support frame comprising the four beams 61A, 62A, 63 and 64 is forming a rectangle and in its reference position. The beams 61A and 62A can move in direction parallel to the axes of the specimen contact rods 50 and 51 relative to each other as the parallelogram linkage support frame parallelograms. The beams of the parallelogram linkage support frame then remain parallel, but the frame moves out of a rectangular shape.

It also should be noted that the openings that are formed in the beams 61 and 62 are for weight reduction, and one such opening 62C is shown in FIG. 7 in cross-section. The weight reduction openings also are provided in the stop members 151 and 153. The parallelogram linkage support frame carries a counterweight 157 to balance the extensometer assembly relative to the support strap 46.

It can thus be seen that the support strap 46 provides a vertical support for the entire parallelogram linkage support frame 60, the sensing system 53 and rod 51, and the support for the upper specimen contact rod 50. The support frame 60 is free to move in direction of the axes 50B and 51B of the specimen contact rods 50 and 51. The specimen contact rods 50 and 51 are urged toward the specimen 11, through a hold down flexure assembly indicated at 170 that provides a spring or biasing load against the base ends of the specimen contact rods 50 and 51, tending to move them toward the specimen. Hold down flexure assembly 170 is also made to accommodate differential axial movement of the specimen contact rods 50 and 51 without substantial restraint (as can the parallelogram linkage support frame), and also twisting of the rods about the axis 132, which axis is also represented in FIG. 1. The parallelogram linkage support frame is urged toward the specimen 11 as well by the hold down flexure assembly 170.

The hold down flexure assembly 170 is supported to one side of the plane of the parallelogram linkage support frame 60 on a removable support slide 171, that is mounted on the upright block 26 of the heat shield 25, as can be seen in FIGS. 1 and 2. Slide 171 supports a first prebent spring 172 at a first end, and as can be seen the spring edges taper outwardly toward its outer end. The lines along the edges of spring 172 preferably converge to a point at axis 132. The outer end of the spring 172 supports a block 173 that extends laterally from spring 172 and has a horizontal shoulder surface 174 on one end and on which a laterally extending base flexure spring 175 is mounted. This base flexure spring 175 is relatively thin, but has a substantial width as can be seen in FIG. 2. The base flexure spring 175 has a long flat flexure spring 176 attached thereto with a suitable clamp block arrangement 177. The ends of springs 175 and 176 are overlapped, and the long flexure spring 176 is positioned to be generally on a plane substantially midway between the specimen contact rods 50 and 51. The planes of springs 175 and 176 are perpendicular to the plane of spring 172.

Elongated flexure 176 is thicker than the base section 175 and it extends laterally toward the parallelogram linkage support frame 60. The outer end of the spring 176 is coupled with a clamp block arrangement 180 to a thin flat flexure spring 182 that is supported on a plane substantially midway between the specimen contact rods 50 and 51, and the spring 182 extends laterally across the plane that is defined by the axes 50B and 51B of the specimen contact rods 50 and 51. An outer end of spring flexure 182 is extended so that the spring flexure 182 extends substantially equal distances on opposite sides of the axis 132 as shown in FIG. 1 between the end that is supported by the support blocks 180 and its outer end. A pair of arm members 183 and 184 are clamped to the outer end of spring flexure 182. The arm members 183 and 184 extend vertically from the plane of the spring flexure 182, and suitable cap screws are used for clamping the two arm sections 183 and 184 together with the spring flexure 182 sandwiched between these arm sections. The arm section 183 in turn supports a specimen rod end contact arm 185 that extends laterally back toward the upper specimen contact rod 50, and it has an end adapter 186 that is provided with an internal conical socket that receives and centers a conical end 50C of the upper specimen contact rod 50.

The lower arm section 184 has a laterally extending flexure strap or spring 190 fixed thereto with a suitable block 191, and which extends back toward the lower specimen contact rod 51. The flexure strap 190 has an adapter 192 at the end thereof adjacent the specimen contact rod 51, and this adapter 192 also has a conical interior socket that receives and centers on a conical end 51C of the specimen contact rod 51. The conical surfaces 50C and 51C are on the remote side of the respective clamps that hold the specimen contact rods on their support arms. Flexure spring 182, arm 185 and flexure strap 190 are positioned between the respective arms supporting the specimen contact rods and the fourth beam 64 of the parallelogram linkage support frame. The lateral arm 185 can be replaced with a flexure strap similar to strap 190, if desired.

The conical seats or sockets in end adapters 186 and 192 have conical surfaces that have a substantially greater included angle than the included angle of the end surfaces 50C and 51C to permit the rods to pivot easily in the sockets. The tips of the conical surfaces on the rods also are founded rather than a sharp point to aid pivoting of rods 50 and 51.

It can thus be seen that if the rods 50 and 51 simultaneously move up and down, the flexure spring 175 in particular will bend about an axis generally parallel to the axes of the rods 50 and 51 to permit this movement without substantial load resisting such movement. It also can be seen that there will be an axial load on the specimen contact rods, for example, in the range of 200 grams total, provided by the adapters 186 and 192, under load from the flexure spring 172, which is prebent so it provides a force when it is planar as shown for urging the specimen contact rods against the specimen 11. The resilient force from spring 172 can be selected to insure proper contact between the rods and the specimen across a wide range of movements.

If the specimen contact rods 50 and 51 tend to move together or apart (as rod 51 pivots for measuring specimen loads, or as support frame 60 parallelograms), the flexure strap 190 will accommodate this movement, and if there is any differential axial movement of the rods 50 and 51, the flexure strap 182 will twist to accommodate it. The flexure strap 182 is centered on the axis 132, and the twisting will be accommodated in this flexure strap (the strap 176 is substantially thicker than the strap 182) so there will not be any substantial unwanted loads encountered.

Thus, the hold down flexure assembly 170 accommodates movements of the specimen contact rods without causing erroneous readings or loads.

The flexure spring 176 passes between a pair of arms indicated at 200,200 which are mounted onto the slider block 171, and the arms 200 have aligned openings 201 therethrough through which a pin can be dropped so that the entire flexure assembly of the flexure can be pulled away from the ends of a specimen contact rod by moving the unit out to a point where the spring 172 is bent from planar configuration, and shows the spring section 176 assumes the position in dotted lines in FIG. 2. Then a pin can be dropped through the openings as shown in dotted lines in FIG. 1, to hold the flexure assembly 170 from engaging the specimen contact rods.

The slider assembly 171 permits in and out (lateral) movement for removal and replacement of the flexure assembly 170 as indicated by the arrow 205. As can be seen in FIGS. 1 and 8, respectively, slide 171 has a center boss 171A, forming a pair of slide ears 171B that are slidably fitted into a receptacle in a mounting block 210. The block 210 is clamped onto the block portion 26 of the heat shield 25. The block 210 is clamped in place with cap screws indicated at 211, and as can be seen the block 210 has a slightly recessed forward surface forming spaces 212 at the top and bottom of the main receptacle in which slide 171 is mounted. The recesses 212 are generally U-shaped spaces so that there are legs extending down along the sides of the block 210 as shown in dotted lines in FIG. 1, to form a center recess 212. Spring blades 214 are supported on the legs formed at the ends of the recess 212 above and below the boss 171A of slide 171, using cap screws 215.

It can be seen that the spring blades 214 extend upwardly so that they will retain the flanges or ears 171B in the receptacle formed in the block 210, and yet will permit the boss 171A to slide between these blades. The blades 214 are then clamped down onto the ears 171B by deflecting the blades into the recesses 212 through the use of clamp cap screws shown in FIG. 1 at 220. This will deflect the spring blades 214 to clamp onto the flanges or ears 171B to hold the slide 171 in position as adjusted.

The hold down flexure assembly 170 is pulled away from the ends of the specimen contact rods in axial direction of the rods, and a pin is inserted through the aligned openings 201. The entire flexure assembly 170 can then be moved to the right in mounting block 210 as shown by arrow 205 so that the hold down flexure assembly 170 can be entirely removed from the mounting block 210 and moved to a location clearing the extensometer assembly. The extensometer assembly 10 then may be removed from its mounting bolt 44 by removing pin 47 and withdrawing the rods 50 and 51 from the furnace and heat shield 25, if desired.

As a summary of the operation, then, as the specimen is heated up, and the specimen supporting grips are also heated the specimen can shift substantially relative to the support of flexure strap 46. The shifting will be accommodated without adding bending strain to the ceramic rods 50 and 51 because the parallelogram linkage support frame can parallelogram in its plane through the flexures 66, 67, 68 and 69 that hingedly connect the parallel beams of the parallel linkage support frame 60 together. Other motions of the specimen contact rods other than relative movement along the loading axis of specimen 11 are also accommodated in the hold down flexure assembly 170, such as differential axial movement of the rods. Torsion of the specimen or twisting of the frame is accommodated by the upper contact rod support system 55 that supports the upper contact rod 50 relative to the first beam 61. An adequate and controlled spring force can be applied axially on the specimen contact rods, without incurring any other loads on specimen contact rods that are unwanted.

Additionally, as the specimen shifts, so that, the rods 50 and 51 are at an angle relative to their supports and the parallelogram linkage support frame 60 has moved out of its rectangular arrangement, as indicated by the scribe marks 155 and 156, the nut 43 can be threaded to adjust the axial position of the support screw 44 and the support strap 46 to bring the scribe marks on the stop column 151 and 153 back into registry, meaning that the parallel linkage frame 60 is rectangular and the test is ready to be conducted. The amount of relative axial movement between the beams 61 and 62 is small. The first and second beam sections 61A and 62A remain parallel, but shift axially to accommodate differential axial movement of the specimen contact rods 50 and 51.

The support frame 60 couples the reference specimen contact rod 50 to the movable rod 51 through a measuring sensor system 53 to provide for strain measurement. The sensing system 53 can be any desired form that permits relative pivoting movement of the rod 51 and provides an output signal indicating such movement. For example, capacitive sensing may be used between counterweight arm 94 and beam section 62A, because there is relative movement between these members, or an LVDT also could be used to sense movement caused by strain in the specimen.

The changing of spacing between the outer ends of the rods 50 and 51 which is the movement in direction along the specimen axis is the movement to be sensed, thus is adequately sensed without having unwanted strains placed on the measuring sensor system 53.

The parallelogram linkage support frame can be rotated 90° from the position shown and the specimen contact rods oriented as shown, that is, spaced apart along the axis 18 of a specimen. The coupling members between rod 50 and beam 61 and the measuring system between rod 51 and beam 62 would be reoriented as needed, but the support frame would still parallelogram to permit differential axial movements of the specimen contact rods.

The rod 50 could also be rigidly coupled to the beam 61 if desired, particularly if the gauge length (the distance between the ends 50B and 51B) was relatively long. Then, the support strap 46 would be replaced with a thin wire or line that would permit twisting of the support frame 60 about both horizontal and vertical axes to accommodate torsional shifting.

The upper specimen contact rod support system 55, which permits movement of the rod 50 caused by torsion in the specimen, can have strain gages or other sensors associated therewith to provide torsional strain measurements. The external support for frame 60 would be modified to insure that the torsional strain loads are reacted properly for accurate measurements.

The heat shields adequately shield the members from excessive heat from the furnace, and suitable cooling can be used in passageways in the heat shields as desired. While a furnace for the specimen is disclosed, other sources of heat can be used and the support system can be used with any specimen, whether heated or not, where shifts or movements of the type described may be a problem.

Preferably, the spacing between the first and second beams of the parallelogram linkage support frame will be equal to, or greater than the spacing between the specimen contact rods.

Although the present invention has been described with reference to preferred embodiments, workers skilled in the art will recognize that changes may be made in form and detail without departing from the spirit and scope of the invention.

What is claimed is:

1. An extensometer apparatus comprising:
a parallelogram linkage support frame for supporting at least two specimen contact means which have outer ends adapted to engage a specimen in spaced locations, and including means for indicating movement of the specimen contact means along the loading axis of such specimen, said parallel linkage support frame including a parallelogram linkage having first and second spaced apart substantially parallel beams, and third and fourth spaced apart substantially parallel beams positioned at right angles to the first and second beams;
means for hingedly coupling the third and fourth beams to the first and second beams at spaced locations thereon, respectively;
means for coupling a first of the specimen contact means to a first beam; and
means for coupling a second of said specimen contact means to the second beam, including means for indicating movement of the outer end of said second specimen contact means in direction along a loading axis of such specimen to be tested, the specimen contact means having axes substantially parallel to the axes of said first and second beams at a reference position of the specimen contact means.

2. The apparatus of claim 1 wherein the means coupling the respective specimen contact means to the first and second beams are positioned on a side of the third beam opposite from the fourth beam, and means for independently supporting the parallelogram linkage support frame relative to an external support fixed with respect to a specimen to be tested.

3. The apparatus as specified in claim 2 wherein the specimen contact means comprise first and second elongated specimen contact rods having outer ends for engaging a specimen and base ends supported by the respective means for coupling and wherein said means for supporting the parallelogram linkage support frame comprises a flexible member extending generally parallel to the third and fourth beams and fixed with respect to one of the first and second beams whereby movements of the parallelogram linkage support frame are substantially unrestrained in directions generally parallel to the direction of extension of the specimen contact rods.

4. The apparatus as specified in claim 3 wherein said flexible member comprises a flexible strap suspended on a side of the first beam opposite from the second beam and positioned above the parallelogram linkage support frame, and means for permitting adjustment of the flexible strap and the position of the parallelogram linkage support frame in direction along the longitudinal length of the flexible strap, which is oriented to be substantially parallel to a loading axis of a specimen to be tested.

5. The apparatus as specified in claim 3 and a cross flexure assembly for mounting the first specimen contact rod to the parallelogram linkage support frame, said cross flexure assembly permitting the first specimen contact rod to pivot about an axis generally perpendicular to the longitudinal length of the first specimen contact rod and substantially parallel to a loading axis of a specimen to be tested.

6. The apparatus as specified in claim 3 and hold down bias means engaging base ends of the specimen contact rods adjacent the means coupling said specimen contact rods to the parallelogram linkage support frame, said hold down bias means comprising a spring flexure assembly having means for bearing against said base ends of the specimen contact rods and urging the specimen contact rods in a direction along the longitudinal length thereof toward a specimen to be tested.

7. The apparatus as specified in claim 6 wherein the specimen contact rods have longitudinal axes along the length thereof and wherein said hold down bias means comprises a spring flexure strap that is flexible about an axis generally parallel to the axes of the specimen contact rods, the spring flexure strap being spaced substantially midway between the axes of such rods and extending from a first side of said rods to a second end on a second side of said rods, and support members extending oppositely from the second end of said spring flexure strap back toward the specimen contact rods, said spring flexure strap having substantially equal lengths extending in both directions perpendicular to a plane passing through the axes of said specimen contact rods.

8. The apparatus as specified in claim 7 wherein the spring flexure strap that extends between the specimen contact rods is supported on the first side of said rods by a second bias means spring section that is of greater stiffness than the spring flexure strap to resist bending about axes parallel to the axes of said specimen contact rods before bending of the spring flexure strap from loads from the specimen contact rods tending to cause such bending of the hold down bias means about axes parallel to the axes of the specimen contact rods.

9. The apparatus as specified in claim 8 wherein said spring flexure strap and said spring section of the bias means are supported by a third spring to a fixed support relative to test apparatus for a specimen to be tested, said third spring being flexible to permit bending movements about an axis generally parallel to a line extending between the specimen contact rods and perpendicular to the axes of the rods.

10. The apparatus as specified in claim 9 wherein the specimen is tested when heated from a heat source and heat shield means between the parallelogram linkage support frame and the heat source, said heat shield means being fixedly coupled to a test load frame providing a fixed reference for the parallelogram linkage support frame, said third spring being attached to said heat shield means, and said means to support the parallelogram linkage support frame also being supported on the heat shield means.

11. The apparatus as specified in claim 10 wherein said test load frame has column members, and means for supporting the heat shield means relative to at least one of the column members of said load frame.

12. The apparatus as specified in claim 6 and means to support said bias means relative to the external support for the parallelogram linkage support frame comprising a slide member releasably secured with respect to said external support and slidably movable in direction transverse to a plane passing through the axes of the specimen contact rods.

13. The apparatus as specified in claim 12 wherein said releasable means comprises a flexible blade positioned to engage the slide member, a blade support flexible member mounted on the external support and having a recess aligned with central portions of said blade, said slide member sliding behind said flexible blade, and means to deflect said flexible blade to engage portions of said slide member to clamp the position of said slide member under friction.

14. The apparatus as specified in claim 1 wherein said third and fourth beams of said parallelogram linkage support frame are connected to the first and second beams by flexure straps forming hinges between the beams forming the parallelogram linkage support frame.

15. The apparatus as specified in claim 14 and stop means mounted on said first and second beams including a first stop column mounted on the first beam and extending in direction toward the second beam, and a second stop column mounted on the second beam of the parallelogram linkage and extending toward the first stop column, said first and second stop columns having interfitting portions which limit the amount of pivoting movement of the first and second beams in direction parallel to the first and second beams.

16. In a high temperature extensometer apparatus for mounting a pair of specimen contact rods that have substantially elongation along longitudinal axes thereof, said specimen contact rods having first ends that engage a specimen to be tested while heated by a heat source in a load frame used for providing desired loads on a specimen, the improvement comprising means for supporting the elongated specimen contact contact rods at second ends thereof and which will permit substantial movements of the first ends of said rods when the specimen changes in position and dimension during the heating process from such a heat source comprising a parallelogram linkage support frame having first and second parallel beams spaced apart in direction of spacing of the specimen contact rods, and being spaced apart at least equal to the spacing of the specimen contact rods, and third and fourth beams that are substantially parallel, spaced apart, and which extend between the first and second beams of the parallelogram linkage support frame, and means to hingedly connect the third and fourth beams to the first and second beams at spaced locations whereby the first and second beams can move in direction along the longitudinal length of the first and second beams and thus parallel to the axes of the elongated specimen contact rods; said first and second beams having sections extending outwardly from the third beam in a direction toward the mounting of said specimen contact rods; means for coupling the specimen contact rods to the outwardly extending ends of the first and second beams, respectively, said means for coupling permitting the outer ends of said specimen contact rods to move relative to each other in directions along a loading axis of a specimen to be tested and including means to sense the amount of the outer ends of said specimen contact rods; said third and fourth beams permitting said first and second beams and said specimen contact rods to move in differentially axial direction of the specimen contact rods a substantial distance without placing substantial axial loads 17. The apparatus as specified in claim 16 and means to support the parallelogram linkage support frame with respect to a support for a specimen engaged by the specimen contact rods without providing substantial restraint to the parallelogram linkage support frame in direction generally parallel to the longitudinal axis of the specimen contact rods. on the specimen contact rods.

18. The apparatus as specified in claim 17 and hold down spring flexure means for providing an axial load on the second ends of said elongated specimen contact rods adjacent a location where the rods are engaged by the means to mount the rods to the first and second beams, said spring flexure means being substantially free to flex about axes other than a bias force axis parallel to the longitudinal axes of the specimen contact rods.

19. The apparatus as specified in claim 18 and a support arm supported with respect to a load frame in which a specimen engaged by the specimen contact rods is mounted, and adjustable means to mount the means to support the parallelogram linkage support frame to permit adjusting the position of the parallelogram linkage support frame in direction substantially parallel to a loading axis of a specimen engaged by the specimen contact rods.

20. Apparatus for use in an extensometer assembly having a pair of specimen contact means having first ends that engage a specimen to be tested in a load frame for providing desired loads on a specimen, the improvement comprising hold down bias means for providing a force on the specimen contact means at second ends of the specimen contact means which will permit substantial movements of the first ends of said specimen contact means when the specimen changes in position and dimensions, said bias means comprising a spring flexure assembly having a spring flexure member, means for mounting a first end of the spring flexure member independently of the specimen contact means, means for bearing against said first ends of the specimen contact means, and means connecting a second end of the spring flexure member to the means for bearing to urge the specimen contact means in a direction toward a specimen to be tested along axis of the specimen contact means.

21. The apparatus as specified in claim 20 wherein said means for connecting comprises a spring flexure strap that is flexible about a first axis generally parallel to the direction of urging of the specimen contact means, the spring flexure strap being spaced substantially midway between such specimen contact means and extending from a first end on a first side of said specimen contact means to a second end on a second side of said specimen contact means, and support members for the means for bearing extending oppositely from the second end of said spring flexure strap back toward the specimen contact means, said spring flexure strap having substantially equal lengths extending in both directions from and perpendicular to a plane passing through the axes of said specimen contact means.

22. The apparatus as specified in claim 21 wherein the first end of the spring flexure strap is supported on a second bias means spring section that is of greater stiffness than the spring flexure strap to resist bending about axes parallel to the axes of said specimen contact means before bending of the spring flexure strap from loads from the specimen contact rods tending to cause such bending of the bias means about axes parallel to the axes of the specimen contact means.

23. The apparatus of claim 22 wherein said means for mounting comprises a mounting block for mounting the spring flexure member, means for removably mounting the mounting block on an independent support, and means carried by the mounting block to releasably hold the spring flexure strap in a released position away from the base ends of the specimen contact means against the bias force of the spring flexure member, said mounting block and the spring flexure assembly being removable from the independent support with the spring flexure strap held in its released position.

24. An extensometer apparatus comprising:
a parallel linkage support frame for supporting at least two specimen contact means which have outer ends adapted to engage a specimen in spaced locations, and including means for indicating movement of the specimen contact means along the loading axis of such specimen, said parallel linkage support frame including a parallelogram linkage having first and second spaced apart substantially parallel beams, and third and fourth spaced apart substantially parallel beams positioned at right angles to the first and second beams;

means for hingedly coupling the third and fourth beams to the first and second beams at spaced locations thereon, comprising flexure straps forming hinges between the third and fourth beams and first and second beams, respectively;

means for coupling a first of the specimen contact means to a first beam;

means for coupling a second of said specimen contact means to the second beam, including means for indicating movement of the outer end of said second specimen contact means in direction along a loading axis of such specimen to be tested, the specimen contact means having axes substantially parallel to the axes of said first and second beams at a reference position of the specimen contact rods; and stop means mounted on said first and second beams including a first stop column mounted on the first beam and extending in direction toward the second beam, and a second stop column mounted on the second beam of the parallelogram linkage and extending toward the first stop column, said first and second stop columns having interfitting portions which limit the amount of pivoting movement of the first and second beams in direction parallel to the first and second beams.

25. The apparatus as specified in claim 24 wherein said first and second stop columns have indicia thereon which indicate when the parallelogram linkage support frame is at substantially a rectangular configuration.

* * * * *

UNITED STATES PATENT AND TRADEMARK OFFICE
CERTIFICATE OF CORRECTION

PATENT NO. : 4,884,456

DATED : December 5, 1989

INVENTOR(S) : Harry R. Meline et al.

It is certified that error appears in the above-identified patent and that said Letters Patent is hereby corrected as shown below:

Column 16, line 20, after "axial loads" insert --on the specimen contact rods--.

Column 16, line 27-28, after "contact rods", delete "on the specimen contact rods".

Signed and Sealed this

First Day of January, 1991

Attest:

HARRY F. MANBECK, JR.

*Attesting Officer*          *Commissioner of Patents and Trademarks*